(12) United States Patent
Swayze et al.

(10) Patent No.: US 8,751,169 B1
(45) Date of Patent: Jun. 10, 2014

(54) SPECTRAL METHOD FOR DETERMINING THE SOURCE OF EXPANDED VERMICULITE INSULATION IN ATTICS AND WALLS

(75) Inventors: Gregg A. Swayze, Littleton, CO (US); Heather A. Lowers, Golden, CO (US); Roger N. Clark, Lakewood, CO (US)

(73) Assignee: The United States of America, as represented by the Secretary of the Department of the Interior, Washington, DC (US)

( * ) Notice: Subject to any disclaimer, the term of this patent is extended or adjusted under 35 U.S.C. 154(b) by 404 days.

(21) Appl. No.: 13/247,682

(22) Filed: Sep. 28, 2011

Related U.S. Application Data

(60) Provisional application No. 61/387,685, filed on Sep. 29, 2010.

(51) Int. Cl.
*G01N 31/00* (2006.01)
*C04B 14/20* (2006.01)
*C04B 14/38* (2006.01)

(52) U.S. Cl.
CPC .............. *C04B 14/20* (2013.01); *C04B 14/202* (2013.01); *C04B 14/38* (2013.01)
USPC .... 702/28; 52/506.02; 52/506.03; 52/747.13; 502/63; 423/239.1; 428/99; 374/5; 73/74

(58) Field of Classification Search
CPC ...... C04B 14/20; C04B 14/202; C04B 14/38; C01J 3/02; C01J 3/0264; G01N 2021/6417; E04B 2001/7683; F27D 1/14; F27D 1/00; G01J 3/0272; G01J 3/0289; G01J 3/443

USPC ............ 702/28; 52/384, 388, 506.02, 506.03, 52/747.13; 502/62, 63, 80, 84; 423/328.3, 423/235, 239.1; 428/552, 99; 524/445; 374/5, 121, 123; 73/74
See application file for complete search history.

(56) References Cited

U.S. PATENT DOCUMENTS

| | | | |
|---|---|---|---|
| 5,539,207 A | 7/1996 | Wong | |
| 6,300,269 B1 * | 10/2001 | Poncelet et al. | 502/63 |
| 6,782,669 B1 * | 8/2004 | Dixon | 52/506.02 |
| 7,244,902 B2 * | 7/2007 | Popp et al. | 209/577 |
| 7,445,377 B2 * | 11/2008 | Lee et al. | 374/5 |

(Continued)

FOREIGN PATENT DOCUMENTS

| | | | |
|---|---|---|---|
| JP | 88000484 B | * | 1/1988 |
| JP | 2008241455 A | * | 10/2008 |

OTHER PUBLICATIONS

Clark, R. N., and Roush, T. L., 1984, Reflectance spectroscopy: Quantitative analysis techniques for remote sensing applications: Journal of Geophysical Research, 89, p. 6329-6340.

(Continued)

*Primary Examiner* — Carol S Tsai
(74) *Attorney, Agent, or Firm* — C. Joan Gilsdorf

(57) ABSTRACT

A method for identifying the source of vermiculite insulation in situ using a portable spectrometer with a light-emitting contact probe and a personal computer. Identification is accomplished using NIR reflectance spectroscopy and absorption band depth ratios to differentiate between vermiculite sources and to test for the presence of amphibole, talc, or serpentine contaminants in vermiculite insulation.

23 Claims, 12 Drawing Sheets

(56) References Cited

U.S. PATENT DOCUMENTS

| | | | |
|---|---|---|---|
| 7,715,002 B2 | 5/2010 | Popp et al. | |
| 2005/0055940 A1* | 3/2005 | Dixon | 52/506.02 |
| 2005/0239941 A1* | 10/2005 | Miyamoto | 524/445 |
| 2008/0191137 A1* | 8/2008 | Poteet et al. | 250/338.1 |
| 2008/0295582 A1* | 12/2008 | Lee et al. | 73/74 |
| 2009/0003407 A1* | 1/2009 | Lee et al. | 374/5 |
| 2009/0046759 A1* | 2/2009 | Lee et al. | 374/5 |
| 2010/0140476 A1 | 6/2010 | Werner et al. | |

OTHER PUBLICATIONS

Wright, K. and Palmer, C., 2008, Geochemical signatures as a tool for vermiculite provenance determination: Idaho National Laboratory, U.S. Department of Energy, INL/EXT-08-14828, 157p. <http://www.inl.gov/technicalpublications/Documents/4096547.pdf> (part 1, pp. 1-20).

Wright, K. and Palmer, C., 2008, Geochemical signatures as a tool for vermiculite provenance determination: Idaho National Laboratory, U.S. Department of Energy, INL/EXT-08-14828, 157p. <http://www.inl.gov/technicalpublications/Documents/4096547.pdf> (part 1, pp. 21-40).

Wright, K. and Palmer, C., 2008, Geochemical signatures as a tool for vermiculite provenance determination: Idaho National Laboratory, U.S. Department of Energy, INL/EXT-08-14828, 157p. <http://www.inl.gov/technicalpublications/Documents/4096547.pdf> (part 1, pp. 41-60).

Wright, K. and Palmer, C., 2008, Geochemical signatures as a tool for vermiculite provenance determination: Idaho National Laboratory, U.S. Department of Energy, INL/EXT-08-14828, 157p. <http://www.inl.gov/technicalpublications/Documents/4096547.pdf> (part 1, pp. 61-80).

Wright, K. and Palmer, C., 2008, Geochemical signatures as a tool for vermiculite provenance determination: Idaho National Laboratory, U.S. Department of Energy, INL/EXT-08-14828, 157p. <http://www.inl.gov/technicalpublications/Documents/4096547.pdf> (part 1, pp. 81-100).

Wright, K. and Palmer, C., 2008, Geochemical signatures as a tool for vermiculite provenance determination: Idaho National Laboratory, U.S. Department of Energy, INL/EXT-08-14828, 157p. <http://www.inl.gov/technicalpublications/Documents/4096547.pdf> (part 1, pp. 101-120).

Wright, K. and Palmer, C., 2008, Geochemical signatures as a tool for vermiculite provenance determination: Idaho National Laboratory, U.S. Department of Energy, INL/EXT-08-14828, 157p. <http://www.inl.gov/technicalpublications/Documents/4096547.pdf> (part 1, pp. 121-140).

Wright, K. and Palmer, C., 2008, Geochemical signatures as a tool for vermiculite provenance determination: Idaho National Laboratory, U.S. Department of Energy, INL/EXT-08-14828, 157p. <http://www.inl.gov/technicalpublications/Documents/4096547.pdf> (part 1, pp. 141-158).

Swayze, Gregg et al., 2009, Determining vermiculite source and amphibole content with IR spectroscopy and electron probe microanalysis, paper presented at 2009 SME Annual Meeting & Exhibit and CMA 111th National Western Mining Conference, Denver, CO, 18p.

Bishop, J. L., A. Lougear, J. Newton, P. T. Doran, H. Froeschl, W. Krner, C. Koeberl, and A. X. Trautwein, 2001, Mineralogical and gerchemical analyses of Antarctic lake sediments: A study of reflectance and Mossbauer spectroscopy and C, N and S isotopes with applications for remote sensing on Mars, Geochimica et Cosmochimica Acta, 65 (17): 2875-2897.

Clark, R.N., T.M. Hoefen, G.A. Swayze, K.E. Livo, G.P. Meeker, S.J. Sutley, S. Wilson, I.K. Brownfield, and J.S. Vance, 2003, Reflectance spectroscopy as a rapid assessment tool for the detection of amphiboles from the Libby, Montana Region, U.S. Geological Survey Open File Report 03-128, 42p.

Crowley, J.K. and Vergo, N., 1988, Near-infrared reflectance spectra of mixtures of kaolin group minerals: use in clay studies, Clays and Clay Min., 36, 310-316.

Frank, D. and Edmond, L., 2001, Feasibility for identifying mineralogical and geochemical tracers for vermiculite deposits: U.S. Environmental Protection Agency, Region 10, Seattle, Washington, EPA 910-R-01-002, 44p.

Gunter, M.E., Singleton, E., Bandli, B.R., Lowers, H.A., and Meeker, G.P., 2005, Differentiation of commercial vermiculite based on statistical analysis of bulk chemical data: Fingerprinting vermiculite from Libby, Montana U.S.A.: American Mineralogist, v. 90, p. 749-754.

Kokaly, R.F. and Clark, R.N., 1999, Spectroscopic determination of leaf biochemistry using band-depth analysis of absorption features and stepwise linear regression, Remote Sensing of Environment, v. 67, pp. 267-287.

Lowers, H.A., and Meeker, G.P., 2004, Electron probe microanalysis as a tool for identifying vermiculite sources: Proceedings of Microscopy and Microanalysis, v. 10, Supplement 2, Microscopy Society of America, Cambridge University Press, p. 904-905. doi.10.1017/S1431927604882461.

Swayze, G.A., Clark, R.N., Sutley, S.J., Hoefen, T.M., Plumlee, G.S., Meeker, G.P., Brownfield, I.K., Livo, K.E., and Morath, L.C., 2006, Spectroscopic and x-ray diffraction analyses of asbestos in the World Trade Center dust: in Gaffney, J.S., and Marley, N.A., eds., Urban Aerosols and Their Impacts: Lessons Learned from the World Trade Center Tragedy, American Chemical Society Symposium Series 919, Oxford University Press, pp. 40-65.

Jamal, 2008, Spectral characterization of graphitic mica schists in southeastern Spain using shortwave and thermal infrared, Enschede, ITC, 89p. (part 1, pp. 1-30).

Jamal, 2008, Spectral characterization of graphitic mica schists in southeastern Spain using shortwave and thermal infrared, Enschede, ITC, 89p. (part 2, pp. 31-45).

Jamal, 2008, Spectral characterization of graphitic mica schists in southeastern Spain using shortwave and thermal infrared, Enschede, ITC, 89p. (part 3, pp. 46-60).

Jamal, 2008, Spectral characterization of graphitic mica schists in southeastern Spain using shortwave and thermal infrared, Enschede, ITC, 89p. (part 4, pp. 61-89).

* cited by examiner

SPECTRAL METHOD FOR DETERMINING THE SOURCE OF EXPANDED VERMICULITE INSULATION IN ATTICS AND WALLS

CROSS-REFERENCE TO RELATED APPLICATION(S)

This application is related to and claims the benefit of priority to Provisional Application U.S. Ser. No. 61/387,685, entitled "A Spectral Method for Determining the Source of Expanded Vermiculite Insulation in Attics and Walls," by Gregg A. Swayze et al., filed Sep. 29, 2010 in the U.S. Patent and Trademark Office, the contents of which are incorporated herein by reference.

STATEMENT OF GOVERNMENT INTEREST

The invention described herein may be manufactured, used, and licensed by or for the U.S. Government for governmental purposes without payment of any royalties thereon.

BACKGROUND

The present invention relates in general to a method for classifying the source of insulation and, in particular, to a method for determining the source of expanded vermiculite insulation used in attics and walls.

There are approximately 1 million homes in the United States that have expanded vermiculite attic insulation (U.S. EPA, 1985). Prior to 1990, there were four sources that produced most of the vermiculite ore used for attic insulation. Three of these are located in the United States in Enoree, S.C.; Louisa, Va.; and Libby, Mont. The fourth is located in Palabora, South Africa. Most of the vermiculite used for attic insulation originated from the Rainy Creek Igneous Complex near Libby, Mont., where fibrous amphiboles were a common mineral contaminant. Ore from the Libby mine supplied up to 80% of the world's vermiculite. The Libby mine closed in 1990.

Over the last decade, health studies in the town of Libby (Peipins et al., 2003; McDonald et al., 2004) and at expansion plants throughout the United States that processed ore from this location revealed a high rate of asbestos-related lung disease among people exposed to the fibrous amphibole potentially contained in the vermiculite insulation. Vermiculite from other commercial sources in the United States and South Africa apparently do not contain fibrous amphibole in significant quantities. There will be a growing demand for vermiculite insulation inspections and source identification as the public becomes aware of the potential health issues posed by exposure to fibrous amphiboles during home improvements or maintenance in areas insulated with vermiculite ore from the Libby mine, or of the liabilities of owning property containing this vermiculite.

SUMMARY

Visually differentiating vermiculites according to their source locations can be difficult. Traditional methods used to determine the source of expanded vermiculite samples involve time-consuming laboratory analysis using microscopic, electron probe microanalysis, x-ray fluorescence, and x-ray methods. These methods involve collection of vermiculite samples from an attic or wall, transport of the potentially hazardous samples to an off-site laboratory, and subsequent analysis to detect amphibole fibers. The methods are costly and generate hazardous waste that must be disposed of properly. In addition, property owners typically get the results of their analyses a week or more after the samples are collected. Thus, improvements are desired in this art.

Given the large number of homes and businesses potentially requiring evaluation for the presence of vermiculite insulation from Libby, use of an in situ analytical method to differentiate among vermiculite sources can save time, eliminate the transport of potentially hazardous vermiculite samples, and reduce analysis costs.

While investigating the spectral properties of vermiculite ore from Libby, Mont., the inventors observed that ultraviolet-near infrared (UV-NIR) spectral examination of expanded vermiculite shows characteristic vibrational absorption features in the 1.4- and 2.3-micron regions that can be used to differentiate among vermiculite sources. These results indicated that portable field spectrometers can be used to make in situ reflectance measurements to determine the source of the vermiculite and to estimate the amount of potentially fibrous amphibole in expanded vermiculite. The inventors realized that spectrally identifying the source of vermiculite would help in evaluating the potential for asbestos contamination. Use of a spectral method for in situ measurement of asbestos contamination in attics and walls insulated with vermiculite would speed the evaluation process by avoiding potentially costly and time-consuming laboratory analysis.

The inventors conducted a study to determine if near-infrared reflectance spectra could be used to identify the source of the vermiculite ore. Spectra of 29 expanded vermiculite samples, including attic insulation, commercial packing material, and horticultural products, were measured with a portable field spectrometer. The sources of the vermiculite samples were distinguished based on differences in elemental composition as measured by electron probe microanalysis and collection location information. Reflectance spectra of the samples have absorptions that vary in wavelength position and relative intensity depending on composition, which allows determination of source and detection of potential amphibole, talc, and/or serpentine contamination.

The resulting in situ spectral method developed by the inventors can be used to identify expanded vermiculite originating from Libby, Mont., which may contain potentially toxic amphibole fibers. Use of this spectral reflectance method for in situ identification of expanded vermiculite can speed the evaluation process by avoiding potentially costly and time-consuming collection of samples and their subsequent laboratory analyses. Reflectance spectra of expanded vermiculite can be measured using a portable spectrometer in situ in the field by a trained field technician. This method can be used to provide an immediate answer to property owners regarding the origin of their expanded vermiculite insulation. If their insulation is from the vermiculite mine in Libby, Mont., based on its mineral spectral signature, then it is likely contaminated with fibrous amphibole and may require remediation. This spectral identification method can also be used in a laboratory to determine the source of expanded vermiculite samples.

In accordance with an embodiment of the invention, there is provided a system and a method of identifying a source of a vermiculite sample in situ. The method includes determining compositional field boundaries for classes of source areas from spectral measurements of vermiculite materials of known origin, according to band depth ratios for absorption bands centered at 1.38 and 2.32 microns. Each source area class has a range of 1.38/2.32-micron band depth ratios, including the following:

Class 1: 0.0000-0.0005,
Class 2: 0.0005-0.0106,
Class 3: 0.0106-0.0418,
Class 4: 0.0418-0.0657, and
Class 5: 0.0657-0.1200.

Next, a plurality of near infrared reflectance spectral measurements are obtained at a plurality of locations within a sample of unknown origin, and the spectral measurements are averaged. Band depths of the averaged spectral measurements are calculated for absorption bands centered at wavelengths of 1.38, 1.40, 1.42, 2.24, 2.32, and 2.38 microns. Band depth ratios are calculated for the 1.38- and 2.32-micron absorption bands (1.38/2.32 ratio), the 2.24- and 2.38-micron absorption bands (2.24/2.38 ratio), and the 1.40- and 1.42-micron absorption bands (1.40/1.42 ratio). The source of the sample is identified by comparing the 1.38/2.32 ratio of the sample to the range of 1.38/2.32 ratios of each source area class to determine into which source area class the sample fits, yielding a classification result that is provided to a user.

The invention also includes a method of testing for the presence and levels of amphibole, talc, and/or serpentine in the sample using the 1.40/1.42-micron band depth ratios, verifying the identification of the source using the 2.24/2.38-micron band depth ratios, and determining whether the identified source is a false positive based on the wavelength position of the 2.24-micron absorption.

BRIEF DESCRIPTION OF THE DRAWINGS

Various aspects and advantages of the present invention will become apparent and more readily appreciated from the following description, appended claims, and accompanying drawings, of which:

DETAILED DESCRIPTION OF THE PREFERRED EMBODIMENTS

The invention described herein uses reflectance spectroscopy and absorption band depth ratios to differentiate between vermiculite sources and to test for the presence of amphibole, serpentine, and/or talc contaminants in attic vermiculite insulation.

Figure 1:
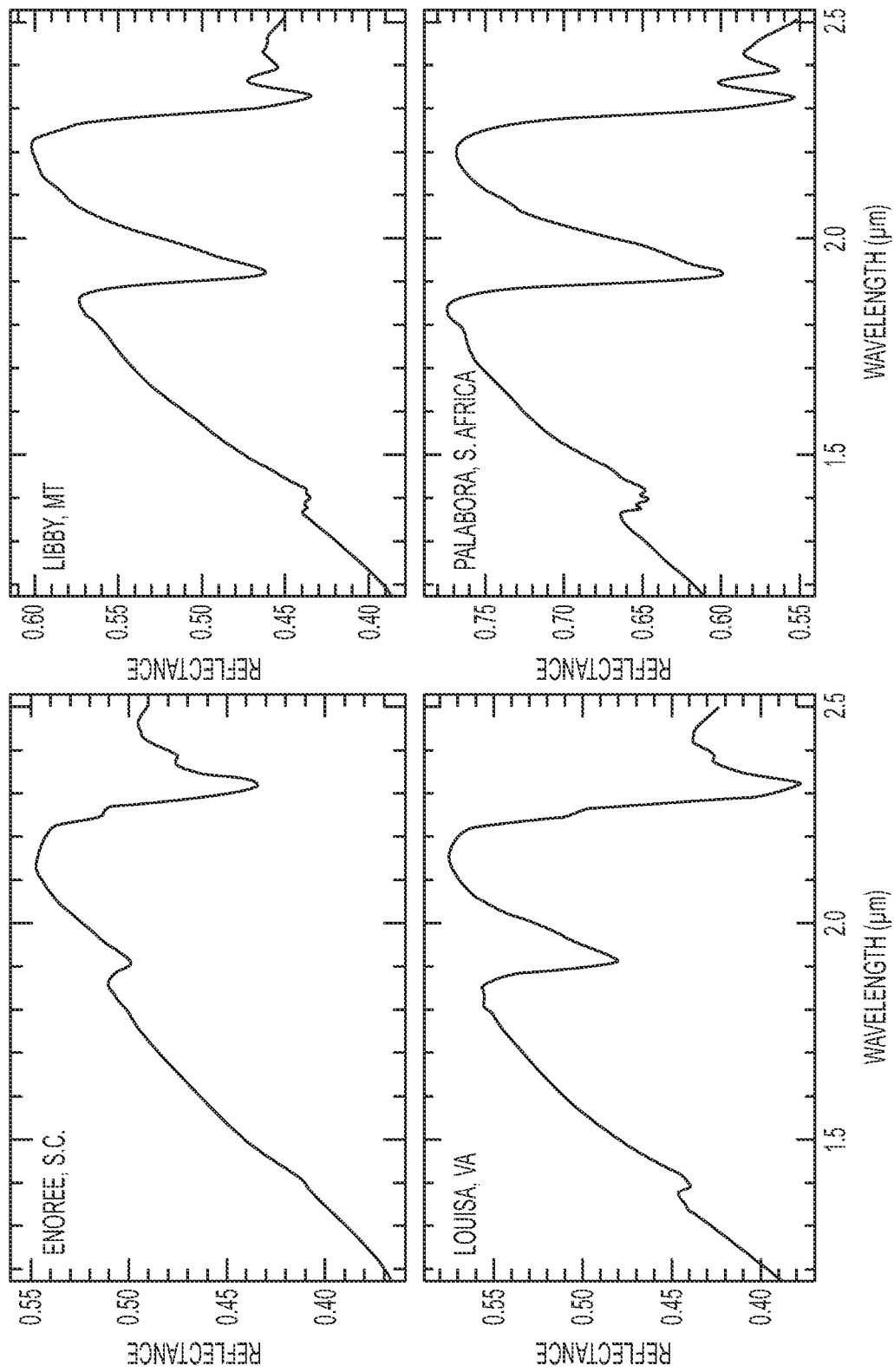
FIG. 1 illustrates near infrared (NIR) reflectance spectra in the wavelength region 1.2 to 2.5 microns of expanded vermiculites from Enoree, S.C.; Libby, Mont.; Louisa, Va.; and Palabora, South Africa.

There are subtle spectral differences in the averaged spectra of Enoree, Libby, Louisa, and Palabora expanded vermiculites that can be used to sort various expanded vermiculite samples according to their respective sources. FIG. 1 shows the averaged spectra of Enoree, Libby, Louisa, and Palabora expanded vermiculites. Vibrational absorption bands in near-infrared (NIR) reflectance spectra of expanded vermiculite change shape and wavelength position as a function of mineral proportions and their elemental composition. In FIG. 1, diagnostic variations can be seen in the 1.4- and 2.3-micron regions: up to 3 bands near 1.4 microns and variable strength of the 2.38-micron band depending on source.

Commercially expanded vermiculite is actually a mixture of the micaceous minerals biotite, hydrobiotite, vermiculite, and impurities in various proportions depending on the source of the ore. These mixtures are herein referred to as "vermiculite." The elemental compositions (e.g., $Fe^{2+}$, $Fe^{3+}$, Mg, Al, O, OH, $H_2O$, and Si) of these individual minerals also change as a function of where they were mined (i.e., their source). The combined effect of variable mineral proportions and elemental compositional changes results in a unique spectral fingerprint for many sources of vermiculite ore. Specifically, band depth ratio values can be used to differentiate vermiculites from different sources and to estimate amphibole, serpentine, and/or talc contamination.

Figure 2:
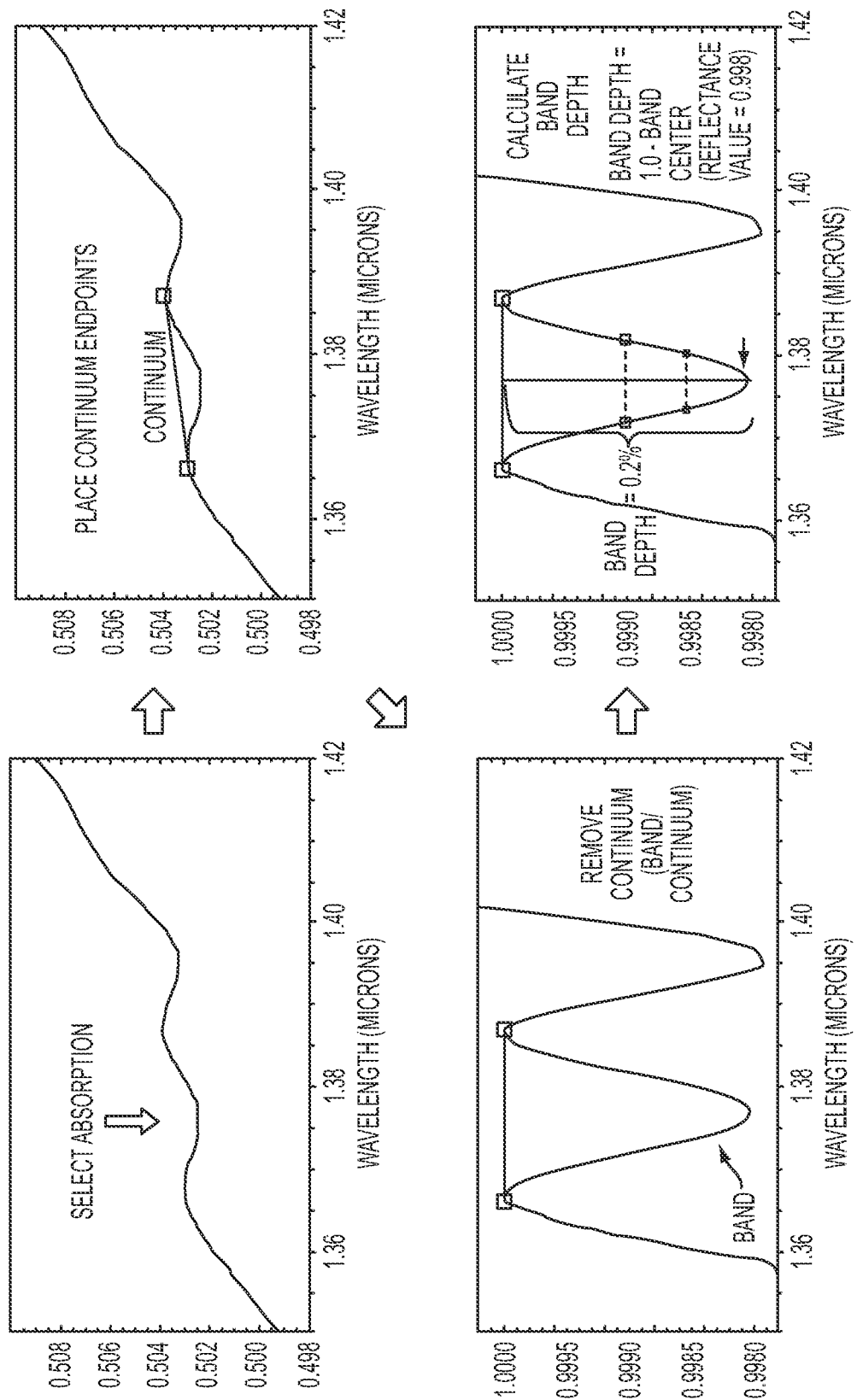
FIG. 2 illustrates measurement of band depth of an absorption band of a NIR reflectance spectrum of expanded vermiculite.

As illustrated in FIG. 2, band depth, which indicates absorption feature strength, is calculated by first normalizing a diagnostic absorption for variations in spectral slope. This is accomplished by dividing the reflectance values of an absorption band by the reflectance values of a straight line continuum drawn between continuum endpoints on the shoulders of the absorption. The reflectance value at the bottom of the normalized absorption is then subtracted from 1.00 to derive the band depth as explained in Clark and Roush (1984). Measuring band depths can be automated if the wavelength locations of the spectral absorptions are known and the data have a signal-to-noise ratio high enough to allow accurate continuum endpoint placement and band depth calculation.

Figure 3:
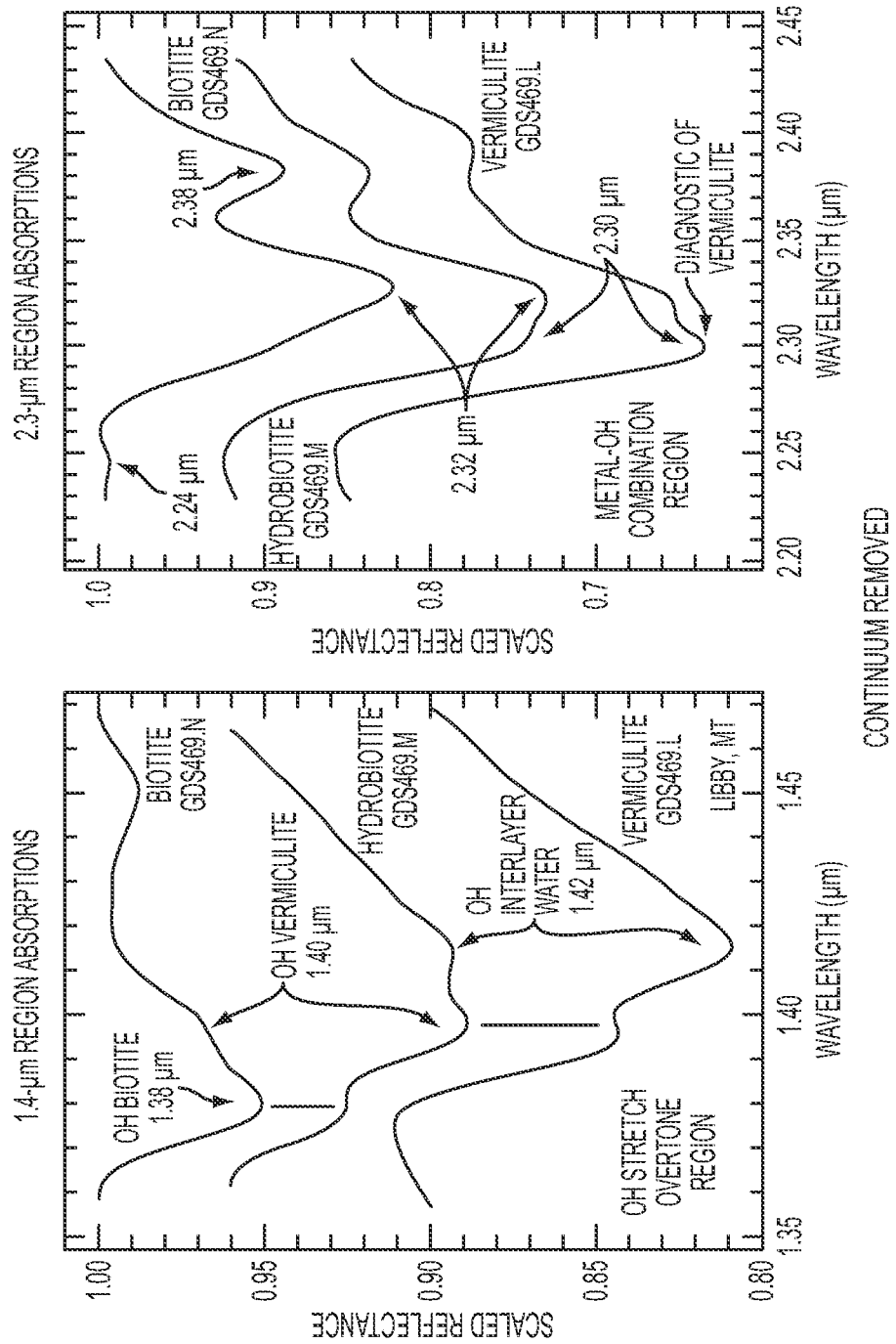
FIG. 3 shows continuum-removed NIR reflectance spectra illustrating 1.4- and 2.3-micron region absorptions for biotite, hydrobiotite, and vermiculite.

FIG. 3 illustrates how diagnostic absorptions are determined. Biotite, hydrobiotite, and vermiculite—the main mineralogic constituents of commercial expanded vermiculite insulation—have diagnostic spectral features in the NIR.

Band depths are calculated for absorptions centered at 1.38, 1.40, 1.42, 2.24, 2.32, and 2.38 microns in spectra compiled by averaging individual spectral measurements at about 20 to 35 different spots within a sample of expanded vermiculite. The absorptions for a sample of Libby expanded vermiculite are shown in FIG. 3. These absorptions are the vibrational absorption overtone and combination bands present in spectra of ground individual flakes of biotite, hydrobiotite, and vermiculite. Intensity variations in them can be used to identify ratio combinations of these minerals and their elemental composition, thus allowing finger printing of sources for vermiculite minerals. The weathering of biotite in the soil can cause biotite to convert to hydrobiotite and then to vermiculite. As biotite is converted to hydrobiotite and vermiculite, new absorption bands grow at the expense of old absorption bands. The presence of a 1.38-micron absorption band is diagnostic of biotite and most hydrobiotites, but is replaced by 1.40- and 1.42-micron bands in vermiculite. The 2.30-micron band is also diagnostic of vermiculite and increases in strength as biotite is converted to vermiculite. Commercial expanded vermiculite is usually a mixture of all three phases in variable proportions.

Figure 4:
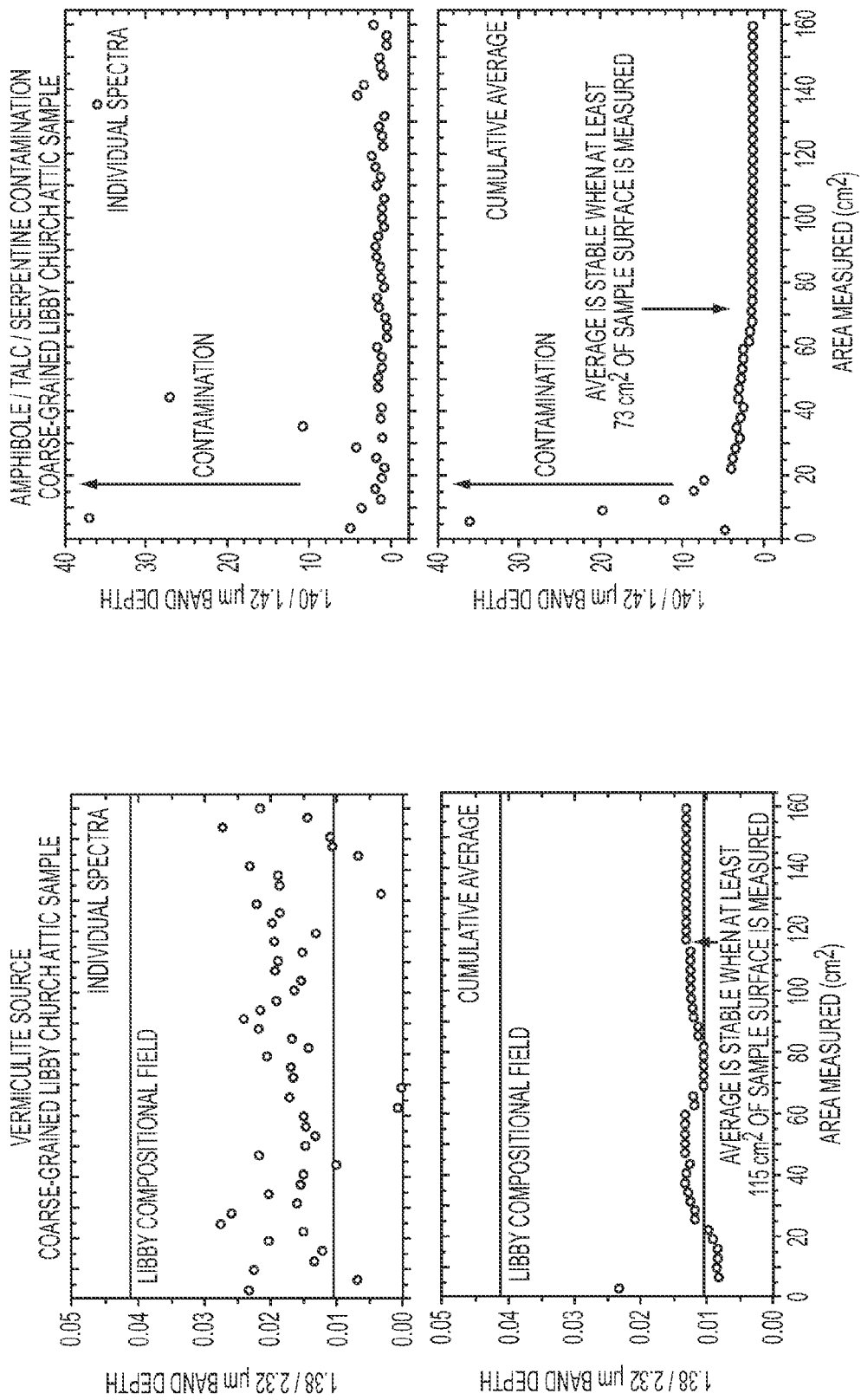
FIG. 4 graphically illustrates determination of the amount of surface area of expanded vermiculite grains that must be measured to accurately derive band depth parameters for coarse-grained expanded vermiculite samples.

FIG. 4 graphically illustrates determination of the amount of surface area of expanded vermiculite grains that must be measured to accurately derive band depth parameters for coarse-grained expanded vermiculite samples. Finer-grained samples require a proportionately smaller surface area for measurement. Coarse vermiculite samples (approximately 1 cm) require more spot measurements because of greater grain-to-grain mineral heterogeneity for a given spectral sampling spot size, than do finer (approximately 1 mm) samples, to achieve reproducible average band depth ratio values (i.e., about 35 spot measurements versus about 20 spot measurements respectively for coarse and fine grained samples). For the vermiculite sample shown in FIG. 4, the cumulative average of band depth ratio values for a coarse-grained vermiculite sample from a church attic in Libby was calculated to assess the total surface area that must be measured to derive accurate band depth parameters. Coarse-grained samples needed the most area measured. For the coarse-grained Libby vermiculite sample, measurement of at least 115 $cm^2$ was needed to accurately determine the source area (i.e., the average becomes stable when at least 115 $cm^2$ of sample surface is measured), while measurement of only 73 $cm^2$ was needed to estimate its average level of amphibole contamination.

Figure 5A:
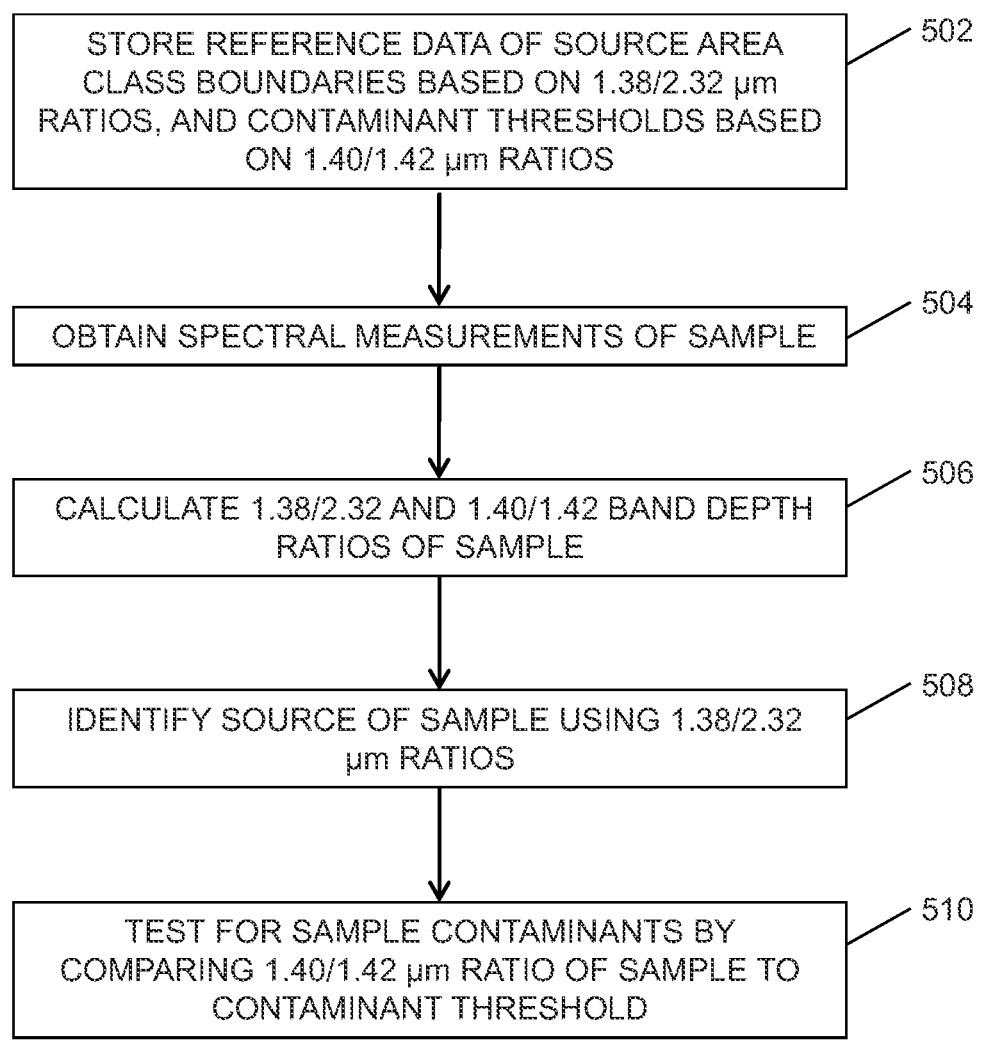
FIG. 5A is a flow chart illustrating identification of the source of expanded vermiculite samples according to 1.38/2.32-micron band depth ratios, and testing for the presence of amphibole, talc, or serpentine contaminants in the samples using 1.40/1.42-micron band depth ratios.

FIG. 5A is a flow chart illustrating identification of the source of expanded vermiculite samples according to 1.38/2.32-micron band depth ratios, and the test for the presence of amphibole, talc, and/or serpentine contaminants in the samples using 1.40/1.42-micron band depth ratios.

First, reference data of source area classes and their boundaries are determined and stored in a table at 502. Spectral measurements of vermiculite materials of known origin are used to generate the reference data. From the spectral measurements of the known materials, band depth ratios are calculated for absorption bands centered at 1.38 and 2.32 microns, which are used to determine the boundaries for each source area. Reference data for the presence of amphibole, talc, and/or serpentine contaminants are also determined and stored in a table based upon band depth ratios calculated for absorption bands centered at 1.40 and 1.42 microns, which are used in conjunction with the 1.38- and 2.32-micron band depth ratios to determine a contaminant boundary or threshold below which no contaminants are detectable.

Next, data are collected at 504 for a sample of unknown origin. NIR reflectance spectral measurements are obtained at a plurality of locations within the sample. Band depth ratios are calculated at 506 from the spectral measurements of the sample for absorption bands centered at wavelengths of 1.38 and 2.32 microns (1.38/2.32 ratio) and at wavelengths of 1.40 and 1.42 microns (1.40/1.42 ratio). The source of the sample is identified at 508 by comparing the 1.38/2.32 ratio of the sample to the table of source area class boundaries to determine into which source area class the sample fits.

The presence of amphibole, talc, and/or serpentine contaminants in the sample is determined at 510 by comparing the 1.40/1.42 ratio of the sample to the threshold. The sample contains contaminants if its 1.40/1.42 ratio is greater than the threshold. A degree of contamination level is determined based upon the magnitude of the 1.40/1.42 ratio of the sample.

Figure 5B:
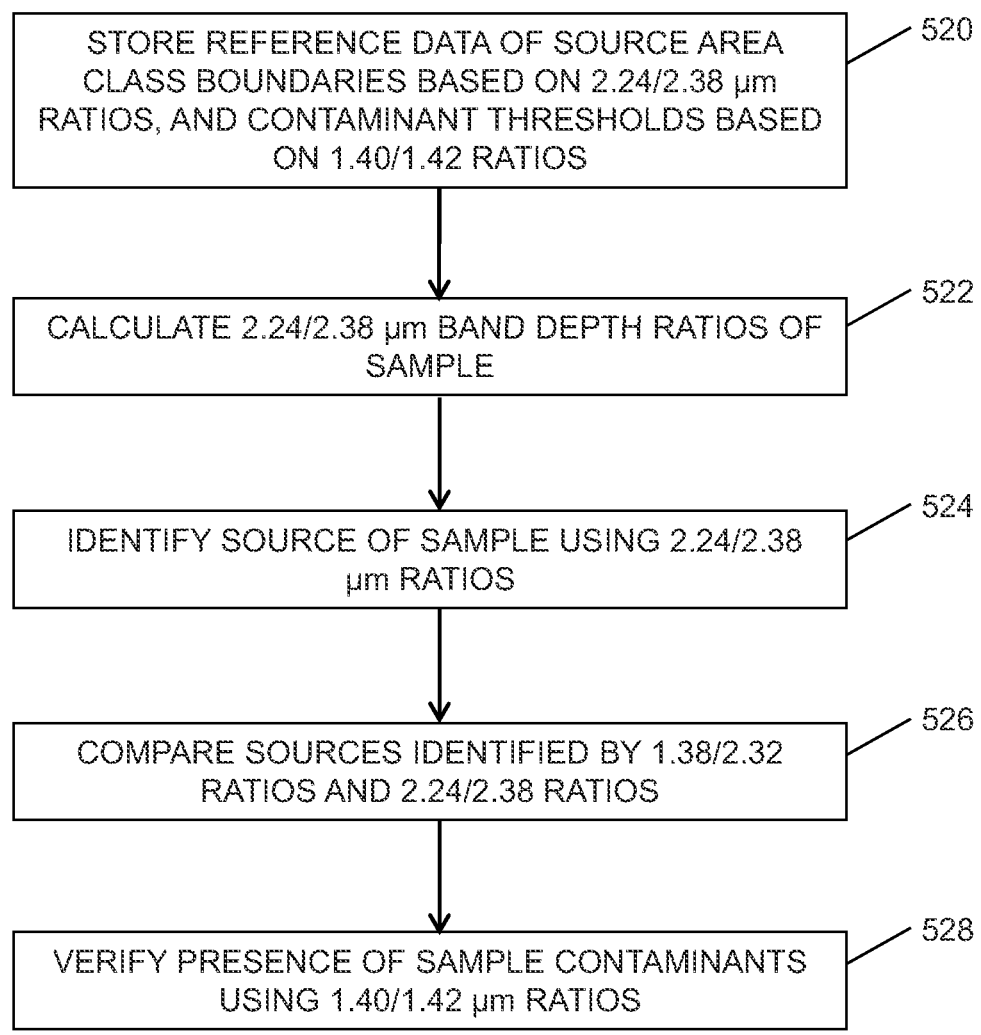
FIG. 5B is a flow chart illustrating verification of the identification of the source of expanded vermiculite samples using 2.24/2.38-micron band depth ratios.

FIG. 5B is a flow chart illustrating verification of the identification of the source of expanded vermiculite samples according to 2.24/2.38-micron band depth ratios, and verification of the presence of amphibole, talc, and/or serpentine contaminants. First, reference data of source area classes and their boundaries based upon 2.24/2.38 ratios are determined and stored in a table at 520. The spectral measurements of vermiculite materials of known origin are used to generate the reference data. From the spectral measurements of the known materials, band depth ratios are calculated for absorption bands centered at 2.24 and 2.38 microns, which are used to determine the boundaries for each source area. Reference data for the presence of amphibole, talc, and/or serpentine contaminants are also determined and stored in a table based upon band depth ratios calculated for absorption bands centered at 1.40 and 1.42 microns, which are used to determine a threshold below which no contaminants are detectable.

Band depth ratios are calculated at 522 from the spectral measurements of the unknown vermiculite sample for absorption bands centered at wavelengths of 2.24 and 2.38 microns (2.24/2.38 ratio) and at wavelengths of 1.40 and 1.42 microns (1.40/1.42 ratio). The source of the sample is identified at 524 by comparing the 2.24/2.38 ratio of the sample to the table of source area class boundaries to determine into which source area class the sample fits. The identification of the source of the sample is verified at 526 by comparing the source area class determined by the 1.38/2.32 ratio method to the source area class determined by the 2.24/2.38 ratio method. If the two source area classes do not match, then standard laboratory techniques (e.g., scanning electron microscopy (SEM), transmission electron microscopy (TEM), or X-ray fluorescence (XRF)) can be used to determine the sample's source area.

The presence of amphibole, talc, and/or serpentine contaminants in the sample is verified at 528 by comparing the 1.40/1.42 ratio of the sample to the threshold. The sample contains contaminants if its 1.40/1.42 ratio is greater than the threshold.

Figure 5C:
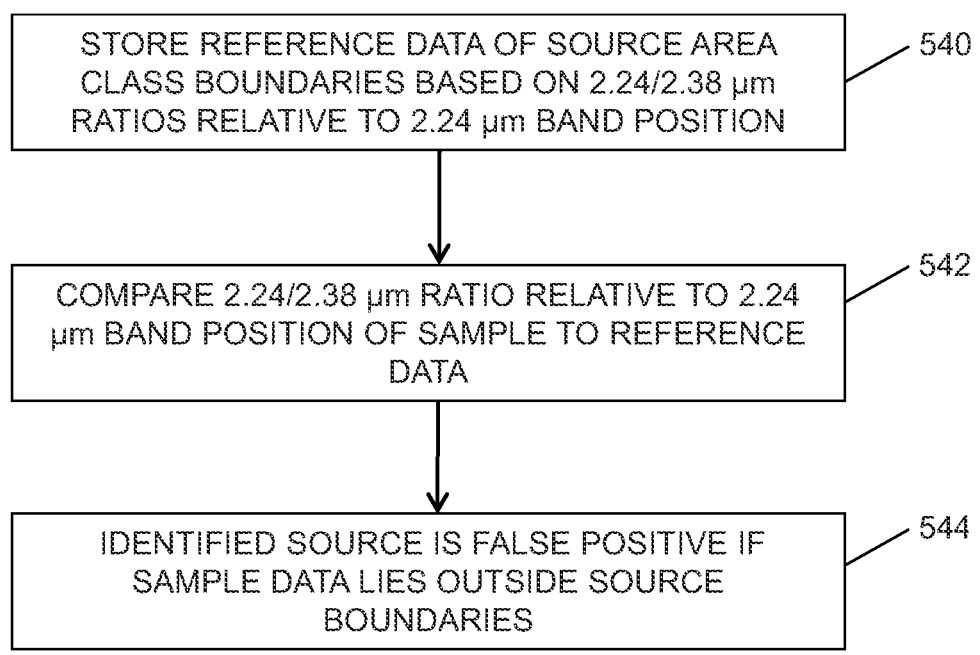
FIG. 5C is a flow chart illustrating determination of whether the identified source is a false positive.

FIG. 5C is a flow chart illustrating determination of whether an identified source is a false positive. The spectral measurements of vermiculite materials of known origin are used to generate at 540 reference data of source area class boundaries based on the 2.24/2.38 ratios relative to the 2.24-micron band position. A determination is made at 542 of whether the identified source is a false positive by comparing the 2.24/2.38 ratio of the sample relative to its 2.24-micron band position to the reference table of source area class boundaries. The identified source is a false positive at 544 if the sample data lies outside the reference boundaries for the source.

Figure 6:
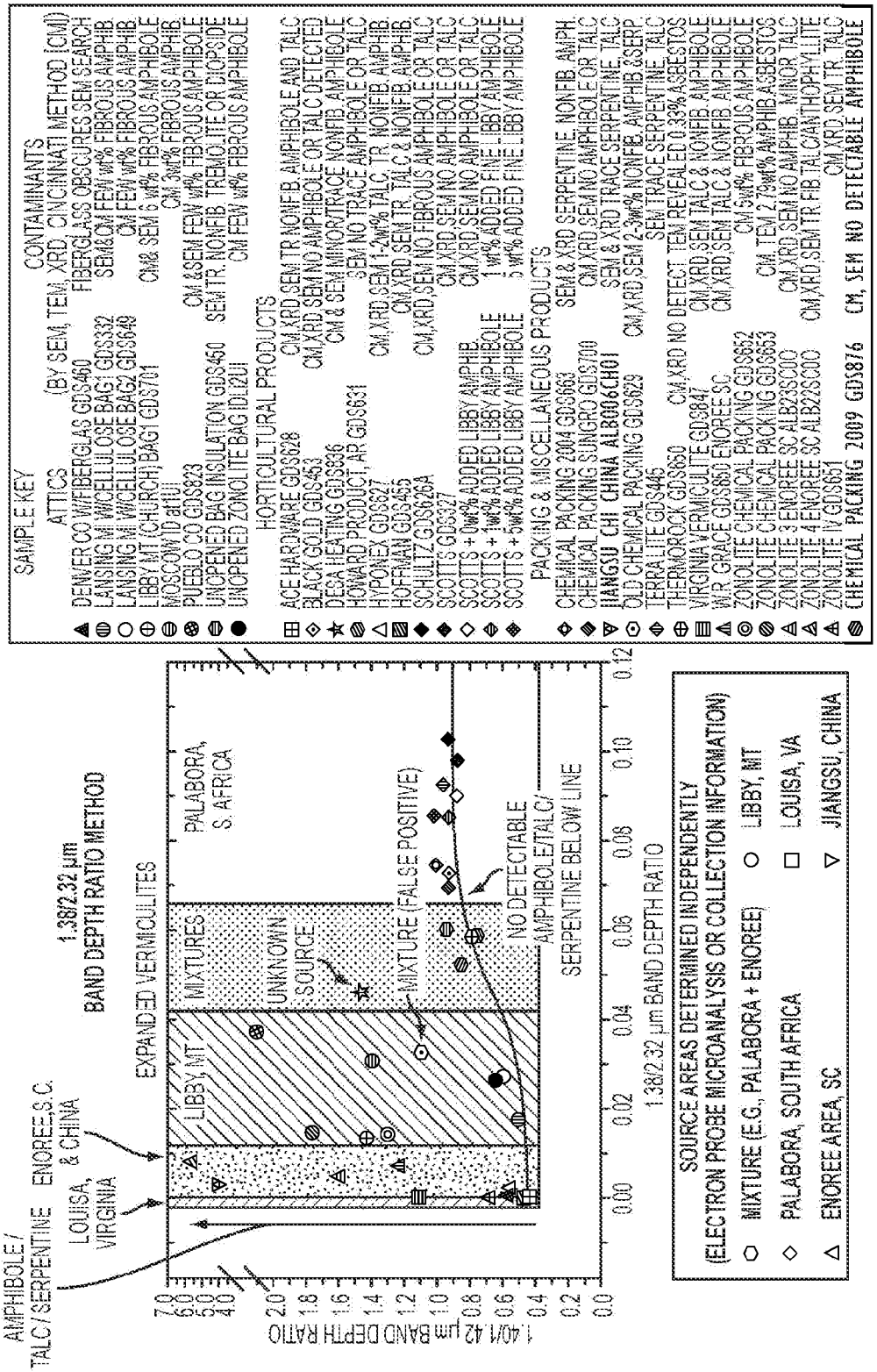
FIG. 6 graphically illustrates the identification of the source of expanded vermiculite samples according to the 1.38/2.32-micron band depth ratios, and the test for the presence of amphibole, talc, or serpentine contaminants in the samples by plotting the 1.38/2.32-micron band depth ratio of each sample relative to its 1.40/1.42-micron band depth ratio.

FIG. 6 graphically illustrates the process of FIG. 5A. Referring to FIG. 6, a plot of the 1.38/2.32 versus 1.40/1.42-micron band depth ratio values for expanded vermiculite samples is used to determine the sources of the vermiculite and potential amphibole, talc, and/or serpentine contamination levels. As discussed above, these diagnostic band depth ratios were determined based on measurements and comparisons to vermiculite materials of known origin. FIG. 6 shows spectral averages of 29 known expanded vermiculite samples from attics, horticultural products, chemical packing, and miscellaneous vermiculite products. Although 32 sample keys are listed in FIG. 6, three of the listings are for laboratory-constructed mixtures of Scotts horticultural vermiculite (manufactured by The Scotts Company of Marysville, Ohio) with known quantities of Libby amphibole. As such they are not "different" samples chemically than the original Scotts sample, so they are not counted with the other samples. A sample from a mine in Jiangsu, China is included to show that as a packing or miscellaneous product, its band ratios plot in the Enoree field, indicating that it has a similar chemistry to expanded vermiculites from Enoree and not to those from Libby. In general, Chinese sources of vermiculite became available as the Libby source closed.

The graph shown in FIG. 6 is divided, according to the 1.38/2.32-micron band depth ratio, into five categories or classes depending upon source area: Louisa, Enoree/China, Libby, Mixtures, and Palabora. The Mixtures category includes mixtures of vermiculites from various sources. The source areas for the 29 vermiculite samples were determined independently using electron probe microanalysis or collection location information. The 29 vermiculite samples were used to empirically determine the boundaries of the source area classes by enclosing clusters of sample points from the same source within boundary lines. For example, for the Libby samples, the minimum and maximum 1.38/2.32-micron band depth ratios determined the boundaries (0.0106 to 0.0418) for the Libby source area. Expanded vermiculite samples from the other source areas fall outside of these bounds. The specific compositional field boundaries for all the categories, expressed as unitless ratios between the 1.38- and 2.32-micron band depths, are as follows:

0.0000-0.0005=Louisa, Va. vermiculites
    0.0005-0.0106=Enoree, S.C. and Jiangsu, China vermiculites
    0.0106-0.0418=Libby, Mont. vermiculites
    0.0418-0.0657=Mixtures of vermiculites from various sources
    0.0657-0.1200=Palabora, South Africa vermiculites Amphibole, talc, and/or serpentine contamination are estimated using the 1.40/1.42-micron band depth ratio. Samples that plot above the curve in FIG. 6 may contain one or more of these contaminant phases. There are no detectable amounts of amphibole, talc, or serpentine in samples that plot below the curve. Non-detect of amphibole, talc, and serpentine was based on spectroscopy and substantiated with SEM, TEM, or X-ray diffraction analysis. Potential amphibole, talc, and/or serpentine contaminants increase the 1.40/1.42-micron band depth ratio for a given sample because these contaminants preferentially absorb photons at 1.40 microns but not at 1.42 microns. Spectroscopy cannot distinguish fibrous from nonfibrous amphibole, talc, and serpentine using this method. Thus, the magnitude of the 1.40/1.42-micron band depth ratio does not necessarily indicate the degree of fibrousness of these potential contaminants; instead, elevated values indicate that amphiboles may be present whether fibrous or not. Direct spectral detection of low levels (less than about 5 wt %) of amphibole in vermiculite is difficult because vermiculite has spectral features at wavelength positions that conceal diagnostic amphibole absorptions. However, when band depths are ratioed, the amphiboles can be detected. Talc and serpentine also have absorptions at nearly the same wavelengths as amphibole, so these vermiculite contaminants cannot be differentiated from amphibole at low concentrations with NIR spectroscopy.

Figure 7:
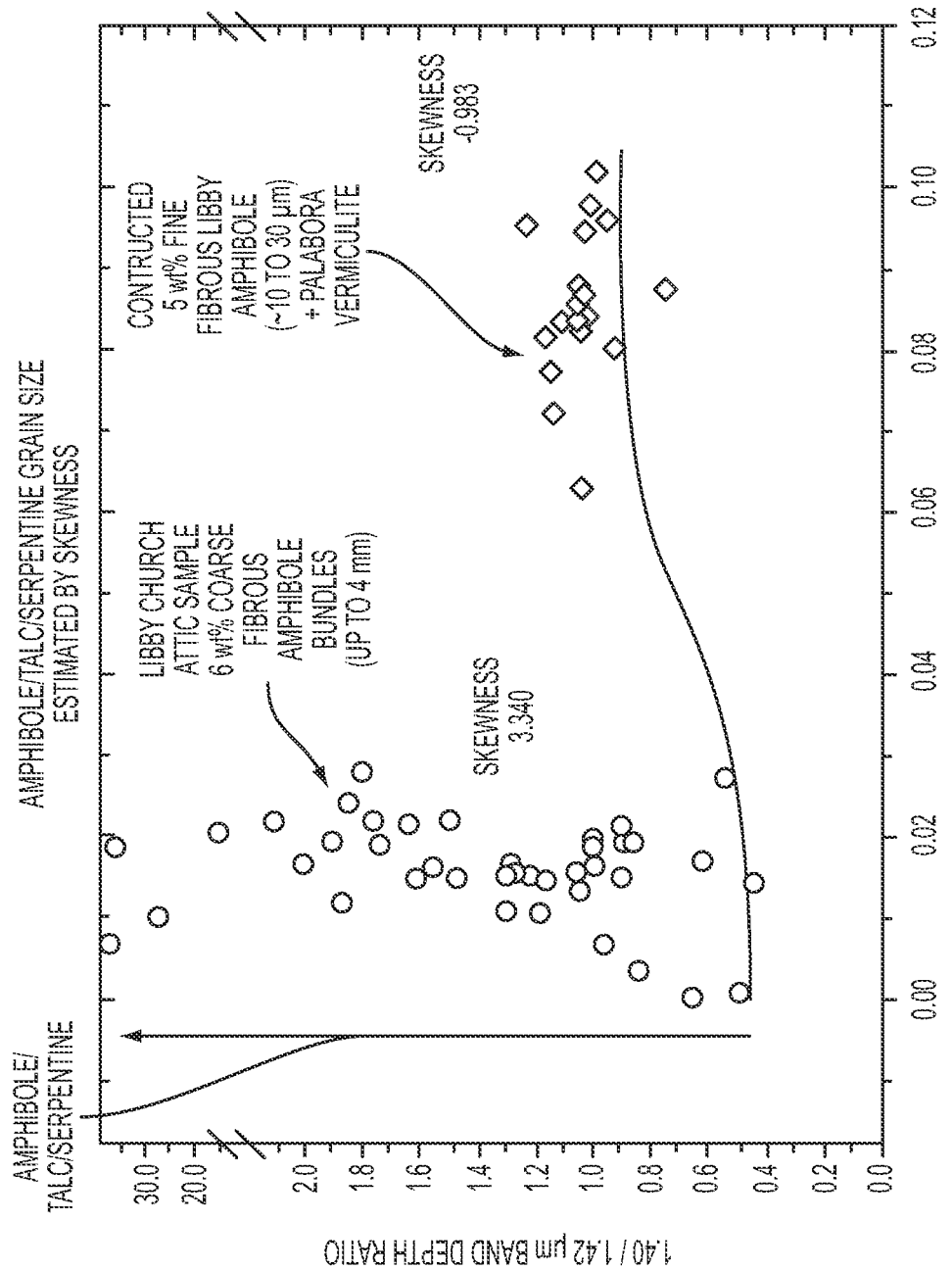
FIG. 7 graphically illustrates the determination of the coarseness of the amphibole, talc, and/or serpentine grains of an expanded vermiculite sample according to the skewness of the 1.40/1.42-micron band depth ratio values for individual spectral measurements of the sample.

Because coarser contaminant grains absorb more strongly than finer contaminant grains, the 1.40/1.42-micron band depth ratio is not a direct measurement of the concentration of these potential contaminants. However, referring to FIG. 7, the skewness of 1.40/1.42-micron band depth ratio values for individual spectral measurements indicates the relative grain size of the contaminants: larger skewness values suggest coarser-grained contaminants while lower values suggest finer-grained contaminants. The circles on the left side of the graph of FIG. 7 represent Libby church attic samples having 6 wt % coarse fibrous amphibole bundles (up to 4 mm). The Libby church attic samples have a skewness of 3.340. The diamonds represent constructed mixtures of 5 wt % fine fibrous Libby amphibole (approximately 10 to 30 microns) with Palabora vermiculite. The constructed vermiculite/amphibole sample has a skewness of −0.983. Note the large positive skewness, or right asymmetry, of the 1.40/1.42-micron band depth parameter distribution shown by the coarser-grained Libby amphibole. This contrasts with the smaller negative skewness of the constructed vermiculite/amphibole mixture. Such differences in skewness values are rough guides to the grain size of amphibole, talc, or serpentine contamination. Contaminant grain size is not always a measure of toxicity. As amphibole bundles from the church attic are disturbed, they can release dangerous individual fibers.

Figure 8:
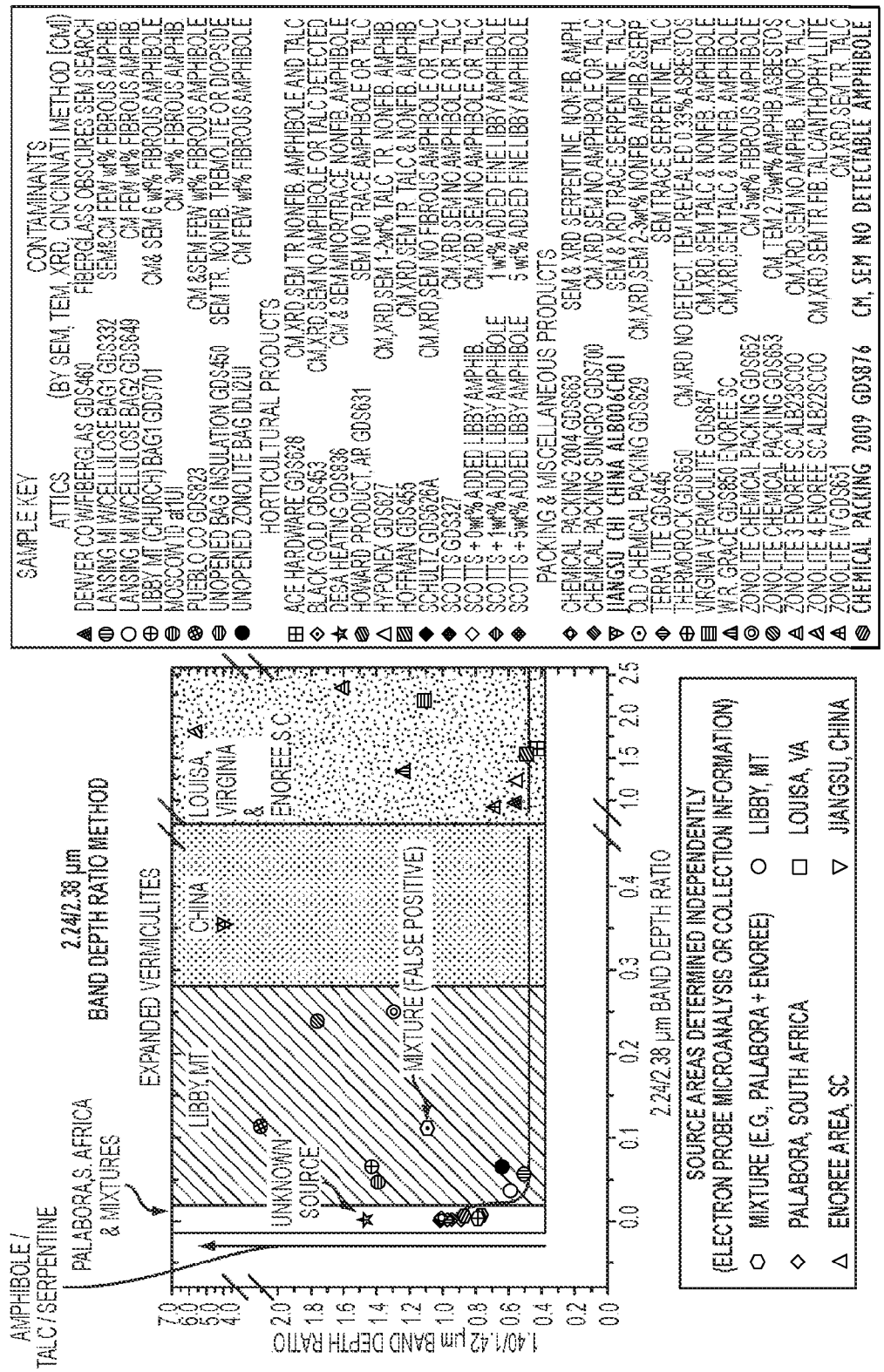
FIG. 8 graphically illustrates the identification of the source of expanded vermiculite samples according to the 2.24/2.38-micron band depth ratios, and the test for the presence of amphibole, talc, or serpentine contaminants in the samples by plotting the 2.24/2.38-micron band depth ratio of each sample relative to its 1.40/1.42-micron band depth ratio.

FIG. 8 graphically illustrates the process of FIG. 5B. FIG. 8 shows a different summary plot of the band depth ratio values for the 29 vermiculite samples discussed above. In FIG. 8, a plot of the 2.24/2.38-versus 1.40/1.42-micron band depth ratio values for expanded vermiculite samples is used to determine the sources of the vermiculite and potential amphibole, talc, and/or serpentine contamination levels. The 29 vermiculite samples were used to empirically determine the boundaries of the source area classes, according to the 2.24/2.38-micron band depth ratios, by enclosing clusters of sample points from the same source within boundary lines. Because there is only one spectrum of the Chinese sample, its boundaries were determined by filling the space between the Libby and Louisa/Enoree fields evenly. The graph is divided into four categories according to the 2.24/2.38-micron band depth ratios. The categories include Palabora/Mixtures, Libby, China, and Louisa/Enoree. FIG. 8 shows that the 2.24/2.38-micron band depth ratio is also sensitive to vermiculite source location. This set of band depth ratios uses only spectral data from the 2.20- to 2.45-micron region to differentiate vermiculite sources. The Libby vermiculites plot at ratioed band depth values between 0.02 and 0.28, and more specifically, between 0.0210 and 0.2832. Data from the 1.40 micron region are again used to estimate potential amphibole, talc, and/or serpentine contamination. The specific compositional field boundaries for the source areas, expressed as unitless ratios between the 2.24- and 2.38-micron band depths, are as follows:

0.0000-0.0210=Palabora South Africa and mixtures of vermiculites
    0.0210-0.2832=Libby, Mont. vermiculites
    0.2832-0.4762=Jiangsu, China vermiculites
    0.4762-2.5000=Louisa, Va. and Enoree, S.C. vermiculites Both the 1.38/2.32- and 2.24/2.38-micron band depth ratio values are sensitive indicators of the source location of the vermiculite and results from both ratios can be compared to check spectral determinations for consistency. The advantage of using the 2.24/2.38-micron band depth ratio values to determine the source of expanded vermiculite insulation is that only spectral data from 2.2 to 2.5 microns need to be collected, unlike the 1.38/2.32-micron band depth ratio values that also require measurement of spectral data in the 1.35- to 1.42-micron region.

Figure 9:
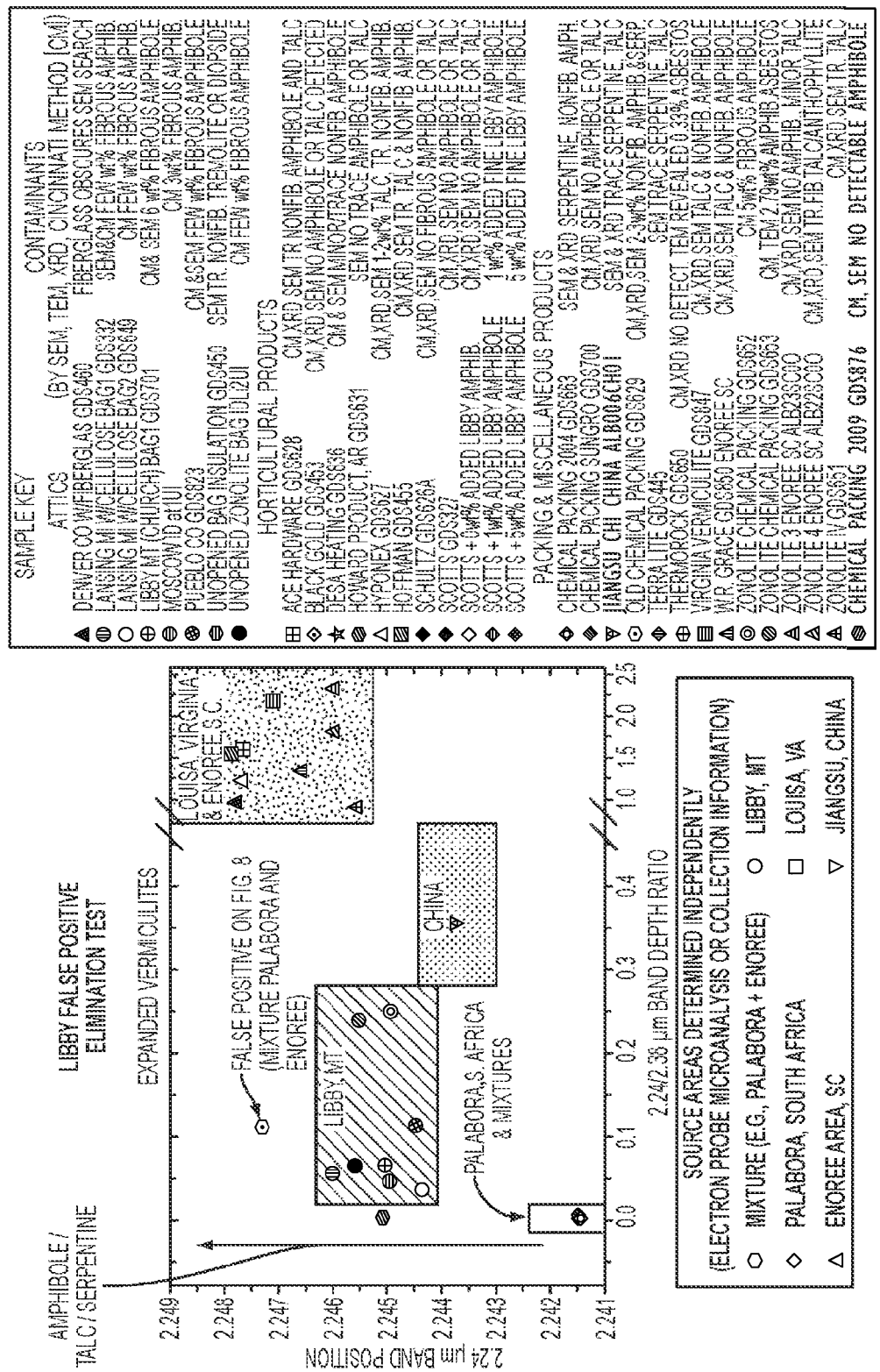
FIG. 9 graphically illustrates the determination of false positive identifications of the source of expanded vermiculite.

FIG. 9 graphically illustrates the process of FIG. 5C of determining false positives. False positive determinations based on the 1.38/2.32 and 2.24/2.38 micron band depth ratio methods can occur when mixtures of vermiculite from sources other than the Libby mine mimic the spectral signature of actual vermiculite from Libby. Referring to FIG. 9, these mixtures can be differentiated from vermiculite samples from Libby by plotting the wavelength position of their 2.24-micron absorptions against their 2.24/2.38-micron band depth ratio values. Because the precise position of the 2.24-micron absorption is controlled by mineral elemental composition, vermiculites from different sources exhibit a range of wavelength positions for this absorption. The 29 vermiculite samples were used to empirically determine the boundaries of the source area classes by enclosing clusters of sample points from the same source within boundary boxes. Even though there is overlap in the position of the 2.24-micron absorption in vermiculites from Libby and Enoree, plotting the position of this absorption against the 2.24/2.38 micron band depth ratio values for samples can reveal the presence of vermiculite mixtures, such as the symbol for the Old Chemical Packing vermiculite sample (which is a Palabora-Enoree mixture), which plots above the box defined by pure Libby samples. The corner coordinates of the box defined by pure Libby samples, where x=2.24/2.38-micron band depth ratio and y=2.24-micron band position in microns, are as follows:

Lower left corner=(0.0186, 2.2441)
Lower right corner=(0.2835, 2.2441)
Upper left corner=(0.0186, 2.2465)
Upper right corner=(0.2835, 2.2465)

Vermiculites with values that plot outside of this box are not from Libby, Mont.

The corner coordinates of the box defined by the Palabora samples are as follows:

Lower left corner=(0.0000, 2.2410)
Lower right corner=(0.0186, 2.2410)
Upper left corner=(0.0000, 2.2424)
Upper right corner=(0.0186, 2.2424)

The corner coordinates of the box defined by the China sample are as follows:

Lower left corner=(0.2835, 2.2431)
Lower right corner=(0.4713, 2.2431)
Upper left corner=(0.2835, 2.2444)
Upper right corner=(0.4713, 2.2444)

The corner coordinates of the box defined by the Louisa/Enoree samples are as follows:

Lower left corner=(0.4713, 2.2453)
Lower right corner=(0.5970, 2.2453)
Upper left corner=(0.4713, 2.2490)
Upper right corner=(0.5970, 2.2490)

No false negative determinations were made for the samples tested. In mixtures where vermiculite from Libby is a minor component, a false negative determination of source could conceivably be made. The likelihood of uniform mixing of Libby vermiculite with other vermiculite in an attic to the point where the Libby spectral signature is lost is small. The method outlined herein calls for sampling attics in a sufficient number of locations (i.e., a minimum of 4 areas with about 5 to 8 spots in each area) to detect patches of unmixed Libby vermiculite, thereby minimizing false negatives. If any Libby vermiculite is detected even once, then a confirmed detection of Libby vermiculite is given for the attic. Samples that fall in the Mixture field category in the 1.38/2.32-micron band depth ratio graph shown in FIG. 6 require an independent test for the presence of fibrous amphibole or serpentine. Moderate levels of cellulose or fiberglass in expanded vermiculite insulation do not affect the spectral source determination because these admixed materials are relatively bright in the NIR while their spectral signatures are dominated by vermiculite.

Figure 10:
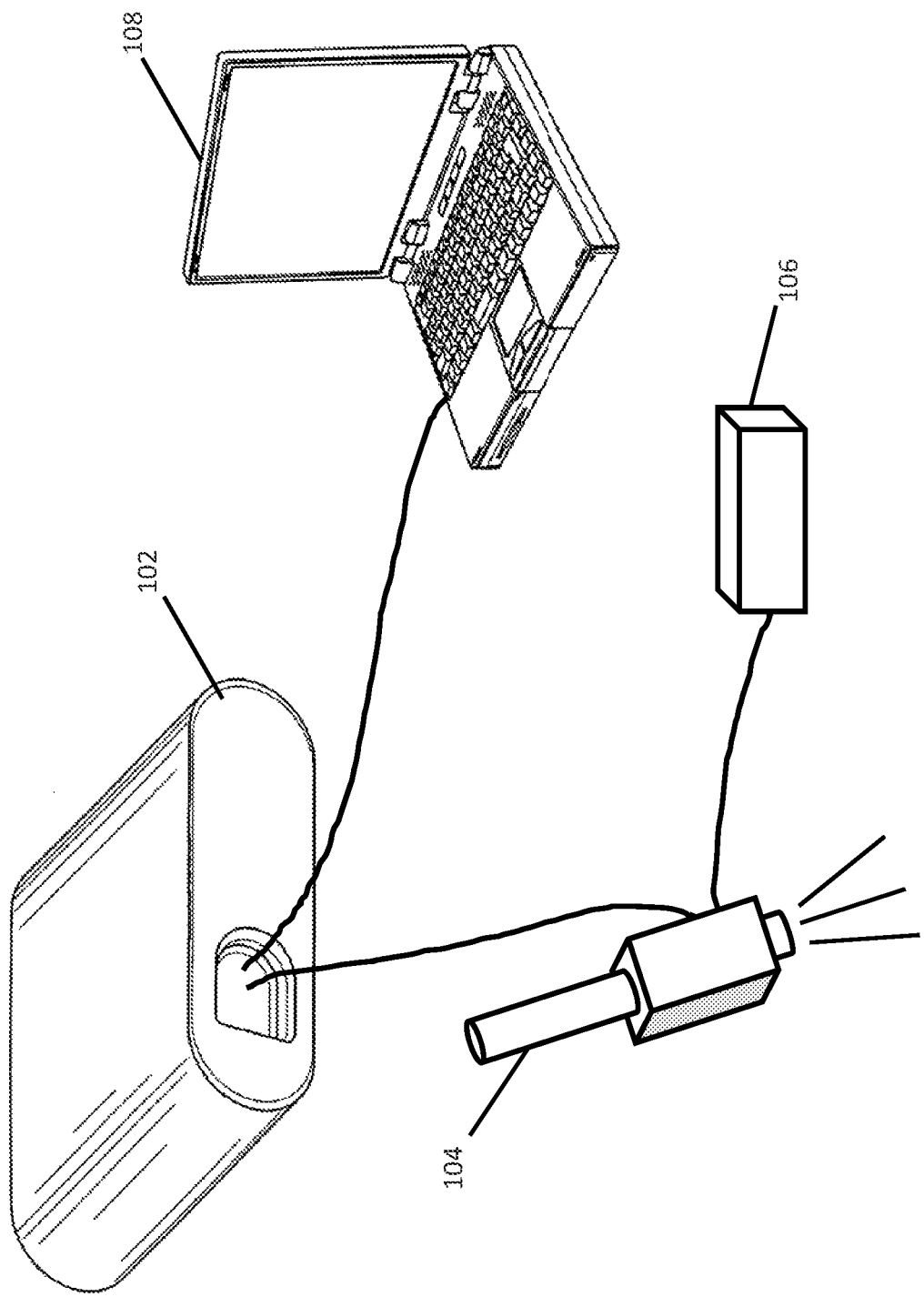
FIG. 10 is a perspective view of an apparatus for obtaining and processing NIR spectral measurements of expanded vermiculite, including a spectrometer with a light contact probe and a controller computing device.

Referring to FIG. 10, a portable field spectrometer 102 equipped with a light emitting contact probe 104 connected to a NiMH battery 106 was used to test the attic insulation, horticultural, packing, and miscellaneous samples discussed above for the presence of expanded vermiculite insulation derived from the Rainy Creek Igneous Complex near Libby, Mont. There are many commercially available portable spectrometers. The spectrometer used for the expanded vermiculite measurements described herein is an ASD, Inc. (Boulder, Colo.) FieldSpec® spectroradiometer with a 1 meter optical fiber and a high intensity contact light probe. Other portable reflectance spectrometers can be used to make these measurements if they have adequate spectral resolution and sampling spot size. For example, a hand-held spectrometer with an internal light rather than a contact probe may be used. A spectral bandpass of 11-nm or smaller with 2-nm spectral sampling is needed to achieve the results shown in FIGS. 4 and 6 to 9. Spot size is herein defined as a 2-cm diameter spot, which was provided during measurements by the optical opening of the ASD Inc. contact light probe. Each spectral measurement was made by inserting the contact probe 104 into an expanded vermiculite sample for a 6-second spectral integration. Care was taken to immerse the probe into the sample where it would only be in contact with expanded vermiculite grains and not the sample container walls.

The spectral measurements made in the field are recorded and analyzed using a controller computer 108 connected to the spectrometer 102. The controller computer 108 has the automated software that continuum-removes the appropriate absorptions and compares their depth ratios, as described above. The software then identifies the likely source of the vermiculite and provides a report outlining the measurements and probable vermiculite source to the operator. A sample configuration includes a personal computer such as a laptop running the Windows® XP operating system with Sigma-Plot® graphing software by Systat Software, Inc. of Chicago, Ill., and reflectance spectroscopy analysis software available from the U.S. Geological Survey.

Advantages of the invention include the ability to perform vermiculite source determinations in situ and to give analytical results to property owners within minutes of the analysis. Potentially hazardous samples need not be collected nor transported to a laboratory for analysis, which is a current requirement for all other methods used to determine the source of vermiculite.

The present invention has been described with respect to the use of NIR reflectance spectroscopy and absorption band depth ratios to differentiate between commercial expanded vermiculite sources. Alternatively, absorption band area ratios can be used in place of band depth ratios to differentiate between vermiculite sources, the source of raw unexpanded vermiculite can be determined using band depth ratio source area classes based on raw vermiculite parameters, and other combinations of band depth ratios can be used to differentiate among vermiculite sources, including those of absorptions in the mid-infrared spectral region.

Thus, it will be appreciated by those skilled in the art that modifications and variations of the present invention are possible without departing from the principles and spirit of the invention, the scope of which is defined in the appended claims and their equivalents.

GENERAL BIBLIOGRAPHY ON THE SUBJECT

The following bibliography provides citations to the references cited in the above text. The references are provided merely to clarify the description of the present invention and citation of a reference either in the bibliography below or in the specification above is not an admission that any such reference is "prior art" to the invention described herein.

Dixon, Gina H., Doria, J., Freed, J. R., Wood, P., May, I., 1985, Exposure assessment for asbestos-contaminated vermiculite: EPA 560/5-85-013, U.S. Environmental Protection Agency, Washington, D.C.

Clark, R. N., and Roush, T. L., 1984, Reflectance spectroscopy: Quantitative analysis techniques for remote sensing applications: *Journal of Geophysical Research,* 89, p. 6329-6340.

McDonald, J. C., Harris, J., Armstrong, B., 2004, Mortality in a cohort of vermiculite miners exposed to fibrous amphibole in Libby, Mont.: Occupational Environmental Medicine, v. 61, p. 363-366.

Peipins, L. A., Lewin, M., Compolucci, S., Lybarger, J. A., Miller, A., Middleton, D., Weis, C., Spence, M., Black, B., and Kapil, V., 2003, Radiographic abnormalities and exposure to asbestos-contaminated vermiculite in the community of Libby, Mont., USA: Environmental Health Perspectives, v. 111, no. 14, p. 1753-1759.

What is claimed is:

1. A method of identifying a source of a vermiculite sample in situ, comprising:
    providing a plurality of source area classes, the source area classes comprising Class 1, Class 2, Class 3, Class 4, and Class 5;
    determining compositional field boundaries for each source area class, from spectral measurements of vermiculite materials of known origin, according to band depth ratios for absorption bands centered at 1.38 and 2.32 microns, each source area class having a range of 1.38/2.32-micron band depth ratios, the range of each source area class comprising:
        Class 1: 0.0000-0.0005,
        Class 2: 0.0005-0.0106,
        Class 3: 0.0106-0.0418,
        Class 4: 0.0418-0.0657,
        Class 5: 0.0657-0.1200;
    obtaining a plurality of near infrared reflectance spectral measurements at a plurality of locations within a sample of unknown origin;
    obtaining an average of the spectral measurements of the sample;
    calculating band depths of the averaged spectral measurements for absorption bands centered at wavelengths of 1.38, 1.40, 1.42, 2.24, 2.32, and 2.38 microns;
    calculating band depth ratios for the 1.38- and 2.32-micron absorption bands (1.38/2.32 ratio), the 2.24- and 2.38-micron absorption bands (2.24/2.38 ratio), and the 1.40- and 1.42-micron absorption bands (1.40/1.42 ratio);
    identifying the source of the sample by comparing the 1.38/2.32 ratio of the sample to the range of 1.38/2.32 ratios of each source area class to determine into which source area class the sample fits to arrive at a classification result; and
    representing the classification result to a user.

2. The method of claim 1, wherein Class 1 is Louisa, Va.; Class 2 is Enoree, S.C. and Jiangsu, China; Class 3 is Libby, Mont.; Class 4 is Mixtures; and Class 5 is Palabora, South Africa.

3. The method of claim 1, further comprising testing for the presence of contaminants in the sample, comprising:
    determining a threshold below which no contaminants are detectable, based upon the 1.38/2.32 and 1.40/1.42 ratios of the vermiculite materials of known origin;
    comparing the 1.40/1.42 ratio of the sample, relative to its 1.38/2.32 ratio, to the threshold;
    determining whether the sample contains contaminants based upon whether the 1.40/1.42 ratio of the sample is greater than the threshold; and
    determining a contamination level of the sample based upon a magnitude of the 1.40/1.42 ratio of the sample.

4. The method of claim 3, wherein the contaminants include amphibole, talc, or serpentine.

5. The method of claim 1, further comprising testing for the presence of contaminants in the sample, comprising:
    generating a graph having an x-axis and a y-axis, where the x-axis=1.38/2.32-micron band depth ratio and the y-axis=1.40/1.42-micron band depth ratio;
    generating a contaminant curve on the graph, based upon the vermiculite materials of known origin, below which no contaminants are detectable;
    plotting a point on the graph of the 1.38/2.32 ratio relative to the 1.40/1.42 ratio of the sample;
    determining whether the sample contains contaminants based upon whether the plotted point lies above or below the contaminant curve; and
    determining a contamination level of the sample based upon a magnitude of the 1.40/1.42 ratio of the sample.

6. The method of claim 5, further comprising determining coarseness of the contaminants, comprising:
    plotting points for each spectral measurement of the sample on the graph;
    calculating a skewness of the plotted points; and
    determining the coarseness of the contaminants based upon the skewness of the plotted points, a positive skewness or right asymmetry indicating a coarse-grained contaminant.

7. The method of claim 1, further comprising verifying the identification of the source, comprising:
    providing additional source area classes, the additional source area classes comprising Class 6, Class 7, Class 8, and Class 9;
    determining compositional field boundaries for each additional source area class from the vermiculite materials of known origin according to band depth ratios for absorption bands centered at 2.24 and 2.38 microns, each additional source area class having a range of 2.24/2.38-micron band depth ratios, the range of each additional source area class comprising:
        Class 6: 0.0000-0.0210,
        Class 7: 0.0210-0.2832,
        Class 8: 0.2832-0.4762,
        Class 9: 0.4762-2.5000;
    identifying the source of the sample by comparing the 2.24/2.38 ratio of the sample to the range of 2.24/2.38 ratios of each additional source area class to determine into which additional source area class the sample fits to arrive at a second classification result;
    verifying the identification of the source by comparing the classification result using the 1.38/2.32 ratios to the second classification result; and representing the second classification and verification result to the user.

8. The method of claim 7, wherein Class 6 is Palabora, South Africa and mixtures; Class 7 is Libby, Mont.; Class 8 is Jiangsu, China; and Class 9 is Louisa, Va. and Enoree, S.C.

9. The method of claim 8, further comprising determining, for an identified source of Libby, Mont., whether the identified source is a false positive, comprising:
determining a Libby source region based upon the 2.24/2.38 ratios relative to the 2.24-micron band positions of the vermiculite materials of known origin; and
determining whether the identified source is a false positive based upon whether the 2.24/2.38 ratio of the sample relative to its 2.24-micron band position is bounded by the Libby source region.

10. The method of claim 8, further comprising determining, for an identified source of Libby, Mont., whether the identified source is a false positive, comprising:
generating a graph having an x-axis and a y-axis, where the x-axis=2.24/2.38 micron band depth ratio and the y-axis=2.24-micron band position;
generating a Libby source region on the graph, the coordinates of the region comprising:
lower left corner: (0.0186, 2.2441),
lower right corner: (0.2835, 2.2441),
upper left corner: (0.0186, 2.2465),
upper right corner: (0.2835, 2.2465);
plotting a point on the graph of the 2.24/2.38 ratio relative to the 2.24-micron band position of the sample; and
determining whether the identified source is a false positive based upon whether the plotted point is within or outside the Libby source region.

11. The method of claim 1, wherein said obtaining a plurality of spectral measurements of a sample comprises obtaining the spectral measurements at about 20 spots within the sample for fine-grained samples and at about 35 spots for coarse-grained samples.

12. The method of claim 1, wherein said obtaining a plurality of spectral measurements of a sample comprises obtaining about 20 to 35 spectral measurements total within the sample.

13. The method of claim 1, wherein the sample is expanded vermiculite.

14. The method of claim 1, wherein the sample is attic insulation.

15. The method of claim 1, wherein said calculating band depth ratios comprises continuum removing each absorption band.

16. A method of identifying a source of a vermiculite sample in situ, comprising:
providing a plurality of source area classes, the source area classes comprising Class 1, Class 2, Class 3, and Class 4;
determining compositional field boundaries for each source area class, from spectral measurements of vermiculite materials of known origin, according to band depth ratios for absorption bands centered at 2.24 and 2.382 microns, each source area class having a range of 2.24/2.38-micron band depth ratios, the range of each source area class comprising:
Class 1: 0.0000-0.0210,
Class 2: 0.0210-0.2832,
Class 3: 0.2832-0.4762,
Class 4: 0.4762-2.5000;
obtaining a plurality of near infrared reflectance spectral measurements at a plurality of locations within a sample of unknown origin;
obtaining an average of the spectral measurements of the sample;
calculating band depths of the averaged spectral measurements for absorption bands centered at wavelengths of 1.38, 1.40, 1.42, 2.24, 2.32, and 2.38 microns;
calculating band depth ratios for the 1.38- and 2.32-micron absorption bands (1.38/2.32 ratio), the 2.24- and 2.38-micron absorption bands (2.24/2.38 ratio), and the 1.40- and 1.42-micron absorption bands (1.40/1.42 ratio);
identifying the source of the sample by comparing the 2.24/2.38 ratio of the sample to the range of 2.24/2.38 ratios of each source area class to determine into which source area class the sample fits to arrive at a classification result; and
representing the classification result to a user.

17. The method of claim 16, further comprising verifying the identification of the source, comprising:
providing additional source area classes, the additional source area classes comprising Class 5, Class 6, Class 7, Class 8, and Class 9;
determining compositional field boundaries for each additional source area class from the vermiculite materials of known origin according to band depth ratios for absorption bands centered at 1.38 and 2.32 microns, each additional source area class having a range of 1.38/2.32-micron band depth ratios, the range of each additional source area class comprising:
Class 5: 0.0000-0.0005,
Class 6: 0.0005-0.0106,
Class 7: 0.0106-0.0418,
Class 8: 0.0418-0.0657,
Class 9: 0.0657-0.1200;
identifying the source of the sample by comparing the 1.38/2.32 ratio of the sample to the range of 1.38/2.32 ratios of each additional source area class to determine into which additional source area class the sample fits to arrive at a second classification result;
verifying the identification of the source by comparing the classification result using the 2.24/2.38 ratios to the second classification result; and
representing the second classification and verification result to the user.

18. The method of claim 16, further comprising testing for the presence of contaminants in the sample, comprising:
determining a threshold below which no contaminants are detectable, based upon the 2.24/2.38 and 1.40/1.42 ratios of the vermiculite materials of known origin;
comparing the 1.40/1.42 ratio of the sample to the threshold;
determining whether the sample contains contaminants based upon whether the 1.40/1.42 ratio of the sample is greater than the threshold; and
determining a contamination level of the sample based upon a magnitude of the 1.40/1.42 ratio of the sample.

19. The method of claim 16, further comprising testing for the presence of contaminants in the sample, comprising:
generating a graph having an x-axis and a y-axis, where the x-axis=2.24/2.38-micron band depth ratio and the y-axis=1.40/1.42-micron band depth ratio;
generating a contaminant curve on the graph, based upon the vermiculite materials of known origin, below which no contaminants are detectable;
plotting a point on the graph of the 2.24/2.38 ratio relative to the 1.40/1.42 ratio of the sample;
determining whether the sample contains contaminants based upon whether the plotted point lies above or below the contaminant curve; and determining a contamination level of the sample based upon a magnitude of the 1.40/1.42 ratio of the sample.

20. A method of identifying a source of a vermiculite sample in situ, comprising:
provided a plurality of source area classes, the source area classes comprising Class 1, Class 2, Class 3, Class 4, and Class 5;
determining compositional field boundaries for each source area class, from spectral measurements of vermiculite materials of known origin, according to band depth ratios for absorption bands centered at 1.38 and 2.32 microns, each source area class having a range of 1.38/2.32-micron band depth ratios, the range of each source area class comprising:
Class 1: 0.0000-0.0005,
Class 2: 0.0005-0.0106,
Class 3: 0.0106-0.0418,
Class 4: 0.0418-0.0657,
Class 5: 0.0657-0.1200;
generating a graph having an x-axis and a y-axis, where the x-axis=1.38/2.32-micron band depth ratio and the y-axis=1.40/1.42-micron band depth ratio;
marking the boundaries of the source area classes on the graph;
obtaining a plurality of near infrared reflectance spectral measurements at a plurality of locations within a sample of unknown origin;
calculating a band depth ratio from the spectral measurements of the sample for an absorption band centered at wavelengths of 1.38 and 2.32 microns (1.38/2.32 ratio) and a band depth ratio for an absorption band centered at wavelengths of 1.40 and 1.42 microns (1.40/1.42 ratio);
plotting a point on the graph of the 1.38/2.32 ratio relative to the 1.40/1.42 ratio of the sample;
identifying the source of the sample by determining which source area class the plotted point falls under to arrive at a classification result; and
testing for the presence of contaminants in the sample, said testing comprising:
generating a contaminant curve on the graph, based upon the vermiculite materials having known origin, below which no contaminants are detectable,
determining whether the sample contains contaminants based upon whether the plotted point lies above or below the contaminant curve, and
determining a contamination level of the sample based upon a magnitude of the 1.40/1.42 ratio of the sample.

21. An apparatus for identifying a source of a vermiculite sample in situ, comprising:
a portable computing device storing compositional field boundaries for each of a plurality of source area classes, the computing device determining the boundaries from spectral measurements of vermiculite materials of known origin, according to band depth ratios for absorption bands centered at 1.38 and 2.32 microns, each source area class having a range of 1.38/2.32-micron band depth ratios, the range of each source area class comprising:
Class 1: 0.0000-0.0005,
Class 2: 0.0005-0.0106,
Class 3: 0.0106-0.0418,
Class 4: 0.0418-0.0657,
Class 5: 0.0657-0.1200;
a portable spectrometer, with a light emitting contact probe, connected to the computing device, the spectrometer obtaining and averaging a plurality of near infrared reflectance spectral measurements at a plurality of locations within the sample, and providing the averaged spectral measurement to the portable computing device, wherein the portable computing device:
calculates band depths of the averaged spectral measurements for absorption bands centered at wavelengths of 1.38, 1.40, 1.42, 2.24, 2.32, and 2.38 microns,
calculates band depth ratios for the 1.38- and 2.32-micron absorption bands (1.38/2.32 ratio), the 2.24- and 2.38-micron absorption bands (2.24/2.38 ratio), and the 1.40- and 1.42-micron absorption bands (1.40/1.42 ratio),
identifies the source of the sample by comparing the 1.38/2.32 ratio of the sample to the range of 1.38/2.32 ratios of each source area class to determine into which source area class the sample fits to arrive at a classification result; and
a display connected to the portable computing device for displaying the classification result to a user.

22. The apparatus of claim 21, wherein the contact probe has a 2-cm diameter spot size and contacts the sample for a 6-second spectral integration.

23. The apparatus of claim 21, wherein the spectrometer has a spectral bandpass of 11-nm or less with 2-nm spectral sampling.

* * * * *